(12) United States Patent
Soleimani et al.

(10) Patent No.: US 12,023,201 B2
(45) Date of Patent: Jul. 2, 2024

(54) METHODS AND APPARATUSES FOR BEAMFORMING IN ULTRASOUND SYSTEMS USING UNBUFFERED DATA SAMPLES

(71) Applicant: BFLY Operations, Inc., Guilford, CT (US)

(72) Inventors: Hamid Soleimani, Guilford, CT (US); Karl Thiele, St. Petersburg, FL (US); Sheng-Wen Huang, Guilford, CT (US); Nevada J. Sanchez, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 49 days.

(21) Appl. No.: 17/236,721

(22) Filed: Apr. 21, 2021

(65) Prior Publication Data

US 2021/0330295 A1 Oct. 28, 2021

Related U.S. Application Data

(60) Provisional application No. 63/013,861, filed on Apr. 22, 2020.

(51) Int. Cl.
*A61B 8/08* (2006.01)
*A61B 8/00* (2006.01)
(Continued)

(52) U.S. Cl.
CPC .......... *A61B 8/5207* (2013.01); *A61B 8/0858* (2013.01); *A61B 8/4494* (2013.01); *G01N 29/0654* (2013.01); *G01S 15/10* (2013.01)

(58) Field of Classification Search
CPC .......... G01S 15/10; G01S 15/06; G01S 15/08; A61B 8/4494
See application file for complete search history.

(56) References Cited

U.S. PATENT DOCUMENTS 4,581,636 A * 4/1986 Blaker .................... G06T 11/40
                                                348/442
4,949,259 A    8/1990 Hunt et al.
(Continued)

FOREIGN PATENT DOCUMENTS

JP    2002143151 A  *  5/2002
JP       3619425 B2  *  2/2005
WO  WO 2019/179758 A1   9/2019

OTHER PUBLICATIONS

JP-2002143151-A (Year: 2002).*
(Continued)

*Primary Examiner* — Joel Lamprecht
*Assistant Examiner* — Nyrobi Celestine
(74) *Attorney, Agent, or Firm* — Carter, DeLuca & Farrell LLP

(57) ABSTRACT

Beamforming circuitry for an ultrasound device is disclosed, that may directly calculate the position in receive line space for an incoming ultrasound data sample given the time of flight (ToF) of that ultrasound data sample. In some embodiments, this may be done without initially buffering the ultrasound data sample received from the particular receive datapath multiplexed to the beamforming circuitry. The beamforming circuitry may then associate the ultrasound data sample with that position in receive line space, and in particular, with a memory address corresponding to that location. Thus, when the beamforming circuitry multiplexes between different receive datapaths, it may not need to buffer ultrasound data samples from different receive datapaths prior to saving the data to memory.

18 Claims, 7 Drawing Sheets

(51) Int. Cl.
    *G01N 29/06*     (2006.01)
    *G01S 15/10*     (2006.01)

(56) References Cited

U.S. PATENT DOCUMENTS

| | | | |
|---|---|---|---|
| 5,345,426 A | 9/1994 | Lipschutz | |
| 5,353,796 A * | 10/1994 | Schroeder | A22B 5/007 73/602 |
| 5,501,219 A * | 3/1996 | Phelps | G01S 7/52025 600/443 |
| 5,522,391 A | 6/1996 | Beaudin et al. | |
| 6,192,164 B1 * | 2/2001 | Park | G01S 7/52044 382/128 |
| 9,521,991 B2 | 12/2016 | Rothberg et al. | |
| 9,592,030 B2 | 3/2017 | Rothberg et al. | |
| 2002/0082500 A1 * | 6/2002 | Henderson | G01S 7/52095 600/443 |
| 2004/0073111 A1 | 4/2004 | Poland et al. | |
| 2006/0074310 A1 | 4/2006 | Thiele | |
| 2006/0173326 A1 | 8/2006 | Thiele | |
| 2006/0197409 A1 | 9/2006 | Thiele | |
| 2007/0032724 A1 | 2/2007 | Thiele | |
| 2008/0024488 A1 | 1/2008 | Visser et al. | |
| 2008/0097204 A1 | 4/2008 | Thiele et al. | |
| 2008/0254925 A1 | 10/2008 | Odabachian et al. | |
| 2008/0288218 A1 | 11/2008 | Thiele | |
| 2009/0007414 A1 * | 1/2009 | Phelps | G01S 7/52096 29/594 |
| 2009/0069692 A1 | 3/2009 | Cooley et al. | |
| 2009/0156935 A1 | 6/2009 | Frisa et al. | |
| 2010/0004540 A1 | 1/2010 | Thiele | |
| 2010/0016725 A1 | 1/2010 | Thiele | |
| 2010/0056921 A1 | 3/2010 | Rafter et al. | |
| 2010/0168580 A1 | 7/2010 | Theile | |
| 2010/0228127 A1 | 9/2010 | Allain et al. | |
| 2011/0319766 A1 * | 12/2011 | Tsuruno | A61B 8/04 600/454 |
| 2012/0034982 A1 | 2/2012 | Felchner et al. | |
| 2012/0121149 A1 * | 5/2012 | Murashita | G06T 3/4069 382/131 |
| 2012/0281902 A1 * | 11/2012 | Oikawa | G01S 7/52034 382/131 |
| 2015/0080728 A1 * | 3/2015 | Uno | G06T 3/4092 345/428 |
| 2015/0153990 A1 | 6/2015 | Rust et al. | |
| 2017/0135676 A1 | 5/2017 | Rothberg et al. | |
| 2017/0258443 A1 | 9/2017 | Rothberg et al. | |
| 2017/0299705 A1 | 10/2017 | Rothberg et al. | |
| 2017/0360399 A1 | 12/2017 | Rothberg et al. | |
| 2017/0360401 A1 | 12/2017 | Rothberg et al. | |
| 2017/0360404 A1 | 12/2017 | Gafner et al. | |
| 2018/0003819 A1 * | 1/2018 | Koptenko | G01N 29/0672 |
| 2018/0011193 A1 * | 1/2018 | Brown | G01S 7/52034 |
| 2018/0120426 A1 | 5/2018 | Thiele | |
| 2018/0367110 A1 * | 12/2018 | Singh | G01N 29/449 |
| 2019/0029651 A1 | 1/2019 | Patil et al. | |
| 2019/0142388 A1 | 5/2019 | Gonyeau et al. | |
| 2019/0307428 A1 | 10/2019 | Silberman et al. | |
| 2019/0343484 A1 | 11/2019 | Rothberg et al. | |
| 2020/0046314 A1 | 2/2020 | Neben et al. | |
| 2020/0129151 A1 | 4/2020 | Neben et al. | |
| 2020/0191928 A1 * | 6/2020 | Hope Simpson | G01S 7/52034 |
| 2020/0315592 A1 | 10/2020 | Soleimani et al. | |
| 2020/0322454 A1 | 10/2020 | Ersson et al. | |
| 2020/0390419 A1 | 12/2020 | Neben et al. | |
| 2020/0405271 A1 | 12/2020 | Chiu et al. | |

OTHER PUBLICATIONS

JP-3619425-B2 (Year: 2005).*
International Search Report and Written Opinion for International Application No. PCT/US2021/028417, mailed Sep. 17, 2021.

* cited by examiner

METHODS AND APPARATUSES FOR BEAMFORMING IN ULTRASOUND SYSTEMS USING UNBUFFERED DATA SAMPLES

CROSS-REFERENCE TO RELATED APPLICATIONS

This application claims the benefit under 35 U.S.C. § 119(e) of U.S. Provisional Patent Application Ser. No. 63/013,861, filed Apr. 22, 2020, entitled "METHODS AND APPARATUSES FOR BEAMFORMING IN ULTRASOUND SYSTEMS," which is hereby incorporated by reference herein in its entirety.

FIELD

Generally, the aspects of the technology described herein relate to ultrasound systems. Some aspects relate to beamforming in ultrasound systems.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to an aspect of the present application, an apparatus is provided, comprising beamforming circuitry configured to calculate a position in receive line space from which an ultrasound data sample was collected using a time-of-flight of the ultrasound data sample as an input.

According to an aspect of the present application, an apparatus is provided, comprising beamforming circuitry configured to calculate a memory address to be updated with an ultrasound data sample using a time-of-flight of the ultrasound data sample as an input.

According to an aspect of the present application, an apparatus is provided, comprising beamforming circuitry configured to multiplex between multiple receive datapaths without buffering ultrasound data samples from the multiple receive datapaths.

According to an aspect of the present application, a method of processing ultrasound data is provided, comprising calculating, with beamforming circuitry, a position in receive line space from which an ultrasound data sample was collected using a time-of-flight of the ultrasound data sample as an input.

According to an aspect of the present application, a method of processing ultrasound data is provided, comprising calculating, using beamforming circuitry, a memory address to be updated with an ultrasound data sample using a time-of-flight of the ultrasound data sample as an input.

According to an aspect of the present application, a method of processing ultrasound data is provided, comprising multiplexing, using beamforming circuitry, between multiple receive datapaths without buffering ultrasound data samples from the multiple receive datapaths.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

In certain types of beamforming circuitry, multiple receive datapaths may be multiplexed to the beamforming circuitry. As the beamforming circuitry multiplexes between the different receive datapaths, it may buffer ultrasound data samples from the different receive datapaths. A time-of-flight (ToF), which may be the time from transmission of an ultrasound wave from an ultrasound device to the time that the reflected ultrasound wave is received by the ultrasound device, may be calculated for each position along a particular receive line (e.g., a multiline). For each position along the receive line, the beamforming circuitry may pull buffered data from one of the receive datapaths that arrived at the calculated ToF corresponding to that position and associate the data with that position along the receive line. The collection of beamformed samples along one or more receive lines associated with one or multiple transmit beams may be referred to as receive line space.

The inventors have developed beamforming circuitry that may directly calculate the position in receive line space for an incoming ultrasound data sample given the ToF of that ultrasound data sample. This may be done without initially buffering the ultrasound data sample received from the particular receive datapath multiplexed to the beamforming circuitry. The beamforming circuitry may then associate the ultrasound data sample with that position in receive line space, and in particular, with a memory address corresponding to that location. Thus, when the beamforming circuitry multiplexes between different receive datapaths, it may not need to buffer ultrasound data samples from different receive datapaths prior to saving the data to memory.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

Figure 1:
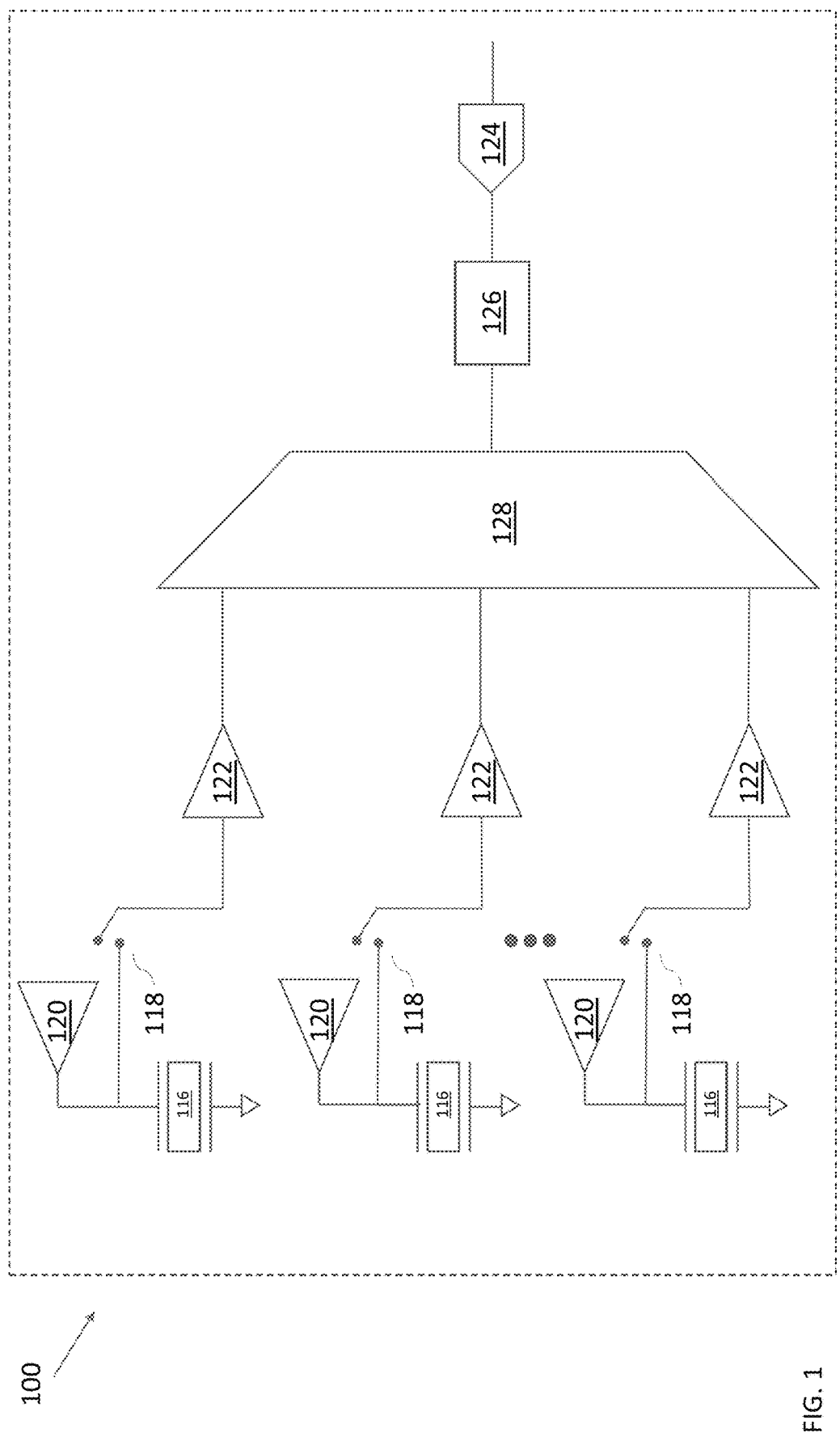
FIG. 1 illustrates a block diagram of an example analog front-end (AFE) in an ultrasound system, in accordance with certain embodiments described herein.

FIG. 1 illustrates a block diagram of an example analog front-end (AFE) 100 in an ultrasound system, in accordance with certain embodiments described herein. The AFE 100 includes ultrasonic transducers 116, receive switches 118, pulsers 120, transimpedance amplifiers 122, an averager 128, analog processing circuitry 126, and an analog-to-digital converters (ADC) 124.

Each pulser 120 is coupled to an ultrasonic transducer 116, which is also coupled, through a receive switch 118, to a transimpedance amplifier 122. The output of each transimpedance amplifier 122 is coupled to the averager 128. The output of the averager 128 is coupled to the analog processing circuitry 126. The output of the analog processing circuitry 126 is coupled to the ADC 124.

Each pulser 120 may be configured to output a driving signal to an ultrasonic transducer 116. The pulser 120 may receive a waveform from a waveform generator (not shown) and be configured to output a driving signal corresponding to the received waveform. When the pulser 120 is driving the ultrasonic transducer 116 (the "transmit phase"), the receive switch 118 may be open such that the driving signal is not applied to the transimpedance amplifier 122.

Each ultrasonic transducer 116 may be configured to emit pulsed ultrasonic signals into a subject, such as a patient, in response to the driving signal received from a pulser 120. The pulsed ultrasonic signals may be back-scattered from structures in the body, such as blood cells or muscular tissue, to produce echoes that return to the ultrasonic transducer 116. The ultrasonic transducer 116 may be configured to convert these echoes into electrical signals. When the ultrasonic transducer 116 is receiving the echoes (the "receive phase"), the receive switch 118 may be closed such that the ultrasonic transducer 116 may transmit the electrical signals representing the received echoes through the receive switch 118 to the transimpedance amplifier 122. The transimpedance amplifier 122 may be configured to convert current signals from the ultrasonic transducer 116 to voltage signals that can be processed by further circuitry in the AFE 100. The averager 128 may be configured to average signals from the different transimpedance amplifiers 122. The averager 128 may be configured to select signals from certain of the transimpedance amplifiers 122 but not others for averaging and outputting. In some embodiments, the averager 128 may be configured to select and output a signal from one transimpedance amplifier 122, without averaging.

The analog processing circuitry 126 may be configured to receive the averaged signal from the averager 128, and may include, for example, one or more analog amplifiers, one or more analog attenuators, one or more analog filters, analog time gain compensation circuitry, and/or ADC driving circuitry. The analog output of the analog processing circuitry 126 output to the ADC 124 for conversion to a digital signal.

In some embodiments, instead of the AFE 100, an AFE may include current-mode analog-to-digital converters (ADCs) configured to directly digitize signals from ultrasound transducers 116.

Figure 2:
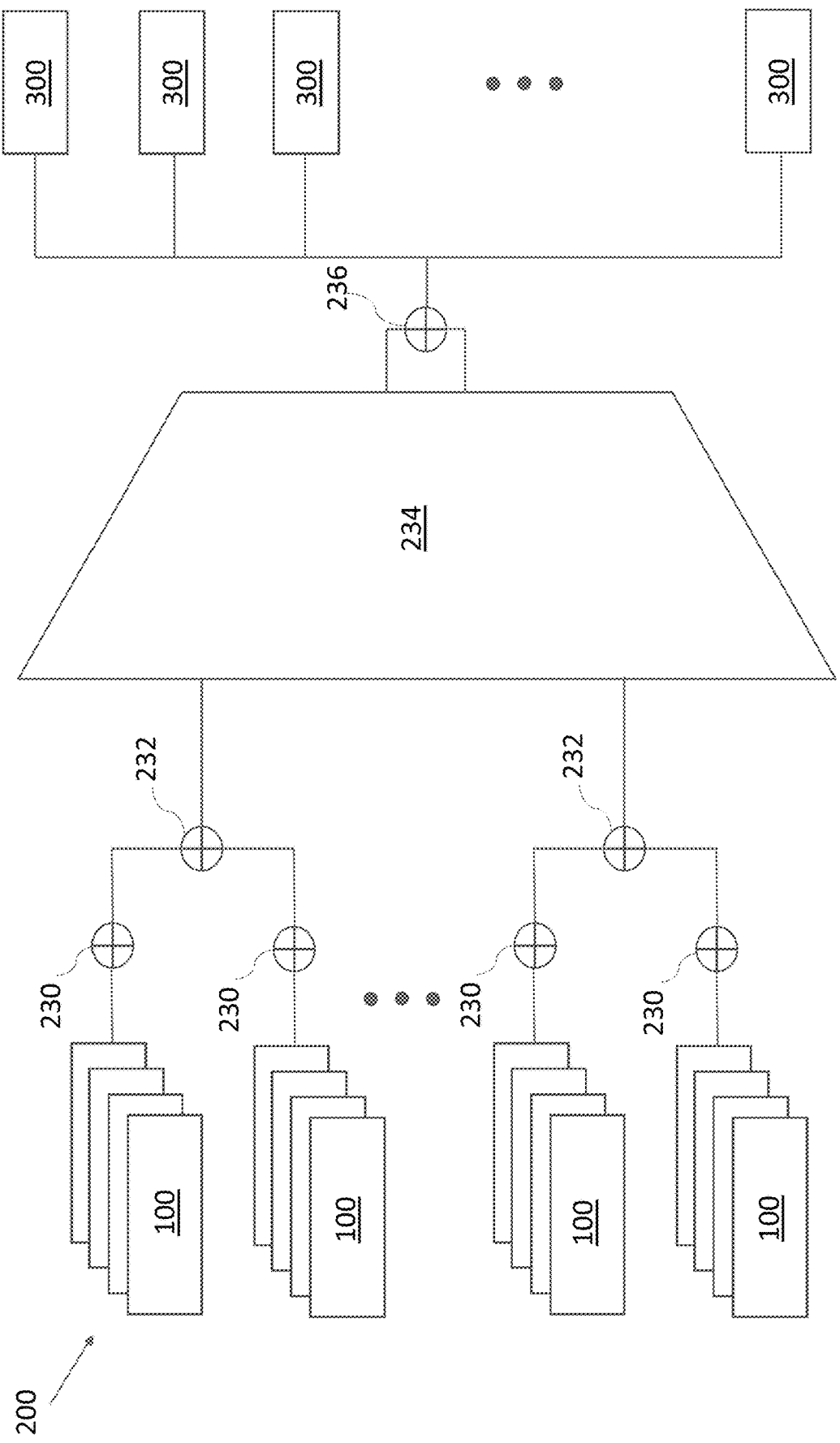
FIG. 2 illustrates a block diagram of an example ultrasound system, in accordance with certain embodiments described herein.

FIG. 2 illustrates a block diagram of an example ultrasound system 200, in accordance with certain embodiments described herein. The ultrasound system includes AFEs 100, summing and/or beamforming circuitry 230, summing circuitry 232, a multiplexer 234, summing circuitry 236, and beamforming circuitry 300.

Multiple AFEs 100 are coupled to an instance of summing and/or beamforming circuitry 230. The outputs of pair of summing and/or beamforming circuitry 230 are coupled to instances of summing circuitry 232, the outputs of which are coupled to the multiplexer 234. Two outputs of the multiplexer 234 are coupled to the summing circuitry 236, the output of which is coupled to multiple instances of the beamforming circuitry 300.

The summing and/or beamforming circuitry 230 may be configured to sum and/or beamform the outputs of ADCs 124 from multiple AFEs 100 (e.g., AFEs 100 in a column of an array of the ultrasound transducers 116). The summing circuitry 232 may be configured to sum the outputs from multiple instances of summing and/or beamforming circuitry 230 (e.g., from the summing and/or beamforming circuitry 230 of two columns). The multiplexer 234 and the summing circuitry 236 may be configured to select and sum, in turn, outputs from pairs of summing circuitry 232. For example, the summing circuitry 236 may sum along the azimuthal dimension of an array of the ultrasound transducers 116. Multiple instances of beamforming circuitry 300 may each receive the output of the summing circuitry 236. On a given cycle of the multiplexer 234, therefore, the multiplexer 234 may output to each instance of beamforming circuitry 300 the output of a different receive datapath. A receive datapath may include all the circuitry (e.g., instances of AFEs 100 (excluding pulsers 120, which are involved in transmission), summing and/or beamforming circuitry 230, and summing circuitry 232) coupled to the summing circuitry 236 through the multiplexer 234 on a given cycle of the multiplexer 234. Each instance of beamforming circuitry 300 may therefore multiplex between different receive datapaths.

In some embodiments, there may be one instance of beamforming circuitry 300 per receive line of ultrasound data. In some embodiments, there may not be summing and/or beamforming circuitry 230. For example, each AFE 100 may be coupled to summing circuitry 232 or directly to the multiplexer 234. In some embodiments, there may not be summing circuitry 232. For example, each summing and/or beamforming circuitry 230 may be coupled directly to the multiplexer 234. In some embodiments, there may not be summing circuitry 236. For example, each instance of beamforming circuitry 300 may be coupled directly to an output of the multiplexer 234. Thus, generally, a datapath may include an ultrasound transducer 116, a transimpedance amplifier 122, analog processing circuitry 126, and an ADC 124.

In addition to the beamforming circuitry 300, the ultrasound system may include further digital processing circuitry, such as one or more digital filters, digital quadrature demodulation (DQDM) circuitry, averaging circuitry, digital dechirp circuitry, digital time delay circuitry, digital phase shifter circuitry, digital summing circuitry, digital multiplying circuitry, requantization circuitry, waveform removal circuitry, image formation circuitry, backend processing circuitry and/or one or more output buffers. The image formation circuitry may be configured to perform apodization, back projection and/or fast hierarchy back projection, interpolation range migration (e.g., Stolt interpolation) or other Fourier resampling techniques, dynamic focusing techniques, delay and sum techniques, tomographic reconstruction techniques, doppler calculation, frequency and spatial compounding, and/or low and high-pass filtering, etc.

Figure 3:
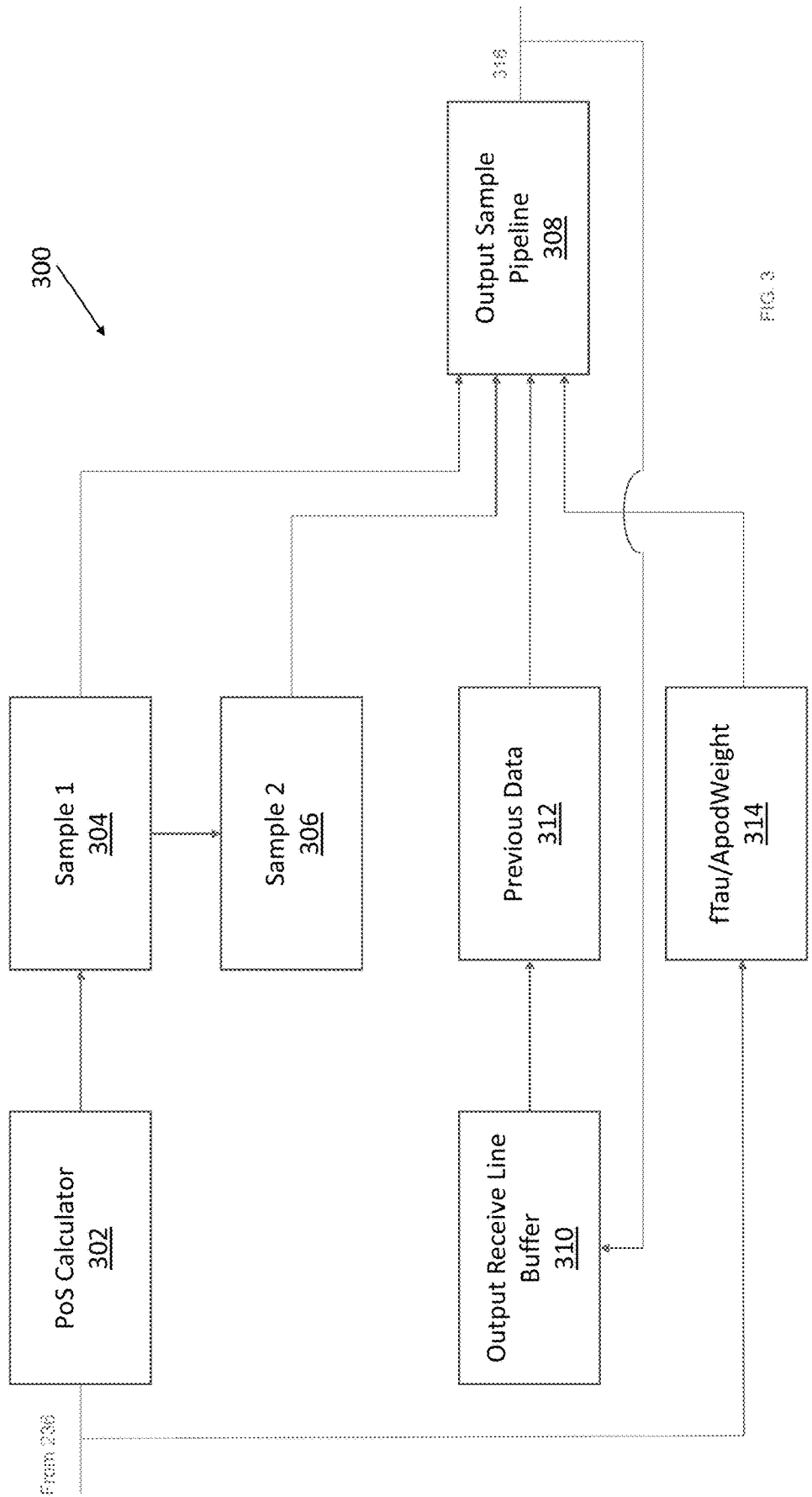
FIG. 3 illustrates a block diagram of an example beamforming system, in accordance with certain embodiments described herein.

FIG. 3 illustrates a block diagram of example beamforming circuitry 300, in accordance with certain embodiments described herein. The beamforming circuitry 300 includes a position-of-sample (PoS) calculator block 302, a sample 1 block 304, a sample 2 block 306, an output sample pipeline block 308 configured to provide an output signal 316, an output receive line buffer block 310, a previous data block 312, and an fTau/ApodWeight block 314.

The input of the PoS calculator block 302, which is also the input of the beamforming circuitry 300, is coupled to an output of a receive datapath (described above with reference to FIG. 2). More particularly, the input of the beamforming circuitry 300 may be multiplexed to multiple different receive datapaths. The output of the PoS calculator block 302 is coupled to the input of the sample 1 block 304. The output of the sample 1 block 304 is coupled to the input of the sample 2 block 306 and to an input of the output sample pipeline block 308. The output of the sample 2 block 306 is coupled to an input of the output sample pipeline block 308. The output of the output sample pipeline block 308 is coupled to the input of the output receive line buffer block 310. The output of the output receive line buffer block 310 is coupled to the input of the previous data block 312. The output of the previous data block 312 is coupled to an input of the output sample pipeline block 308. The input of the fTau/ApodWeight block 314 is coupled to the output of a receive datapath (more particularly, the input of the fTau/ApodWeight block 314 is multiplexed to multiple different receive datapaths). The output of the fTau/ApodWeight block 314 is coupled to an input of the output sample pipeline block 308. The output sample pipeline block 308 provides an output signal 316.

A receive line may include ultrasound data for multiple positions in space. The ultrasound data for each position in space along a particular receive line may be stored at a memory address. In some embodiments, memory addresses may be allocated based on position in space. If, for example, there are N memory addresses for a particular receive line, and depth is the imaging depth, then each memory address may represent a position in space that is depth/N away from the position represented by the previous memory address. The PoS calculator block 302 may be configured to calculate, using the time-of-flight (ToF) of an ultrasound data sample as an input, a position in space along a particular receive line from which the ultrasound data sample was collected. ToF may refer to the time from transmission of an ultrasound wave from an ultrasound device to the time that the reflected ultrasound wave is received by the ultrasound device. The output receive line buffer block 310 may be configured to store ultrasound data for each of the memory addresses for a particular receive line.

For a particular ultrasound data sample, the PoS calculator block 302 may calculate a non-integer memory address. Thus, the ultrasound data sample may not have arrived from a position that exactly corresponds to a position in the receive line space represented by an actual memory address (which is an integer). The beamforming circuitry 300 may be configured to interpolate ultrasound data samples from two different positions around a position in the receive line space represented by an actual memory address to produce a single ultrasound data value to update ultrasound data at that memory address. For example, the PoS calculator block 302 may calculate a memory address of 0.9 for one ultrasound data sample and a location of 1.3 for the next ultrasound data sample. The beamforming circuitry 300 may be configured to interpolate these two ultrasound data samples to produce a single ultrasound data value to update the receive line data in memory address 1. The sample 1 block 304 may be configured to store an incoming ultrasound data sample and output the previous ultrasound data sample to the sample 2 block 306. The ultrasound data samples from the sample 1 block 304 and the sample 2 block 306 may be output to the output sample pipeline block 308 for interpolation by the output sample pipeline block 308. In some embodiments, the interpolation may be linear. In some embodiments, the interpolation may be higher order than linear (e.g., cubic), and the beamforming circuitry 300 may include more than two sample blocks (i.e., more than the sample 1 block 304 and the sample 2 block 306).

In addition to interpolation, the output sample pipeline block 308 may be configured to perform phase correction and apodization. To perform the phase correction and apodization, the output sample pipeline 308 may use parameters fTau and ApodWeight that are received from the fTau/ApodWeight block 314. The fTau/ApodWeight block 314 may calculate these parameters based on the ultrasound data samples from the receive datapath and/or from the PoS value calculated by the PoS calculator block 302. After performing the interpolation, phase correction, and apodization, the output sample pipeline block 308 may be configured to update the resulting receive line sample with the value that was previously at the receive line sample's corresponding memory address. The updating may include accumulation. In particular, the previous data block 312 may be configured to retrieve, from the output receive line buffer block 310, the value that was previously at this memory address and output this value to the output sample pipeline block 308 for accumulation. The accumulation may include accumulating data received from the same spatial location by different ultrasonic transducer elements and/or compounding current receive lines with the next receive lines coherently (i.e., data collected along the same receive line following different transmit events). The output sample pipeline block 308 may be configured to output the accumulated value to the output receive line buffer block 310 to be stored.

Figure 4:
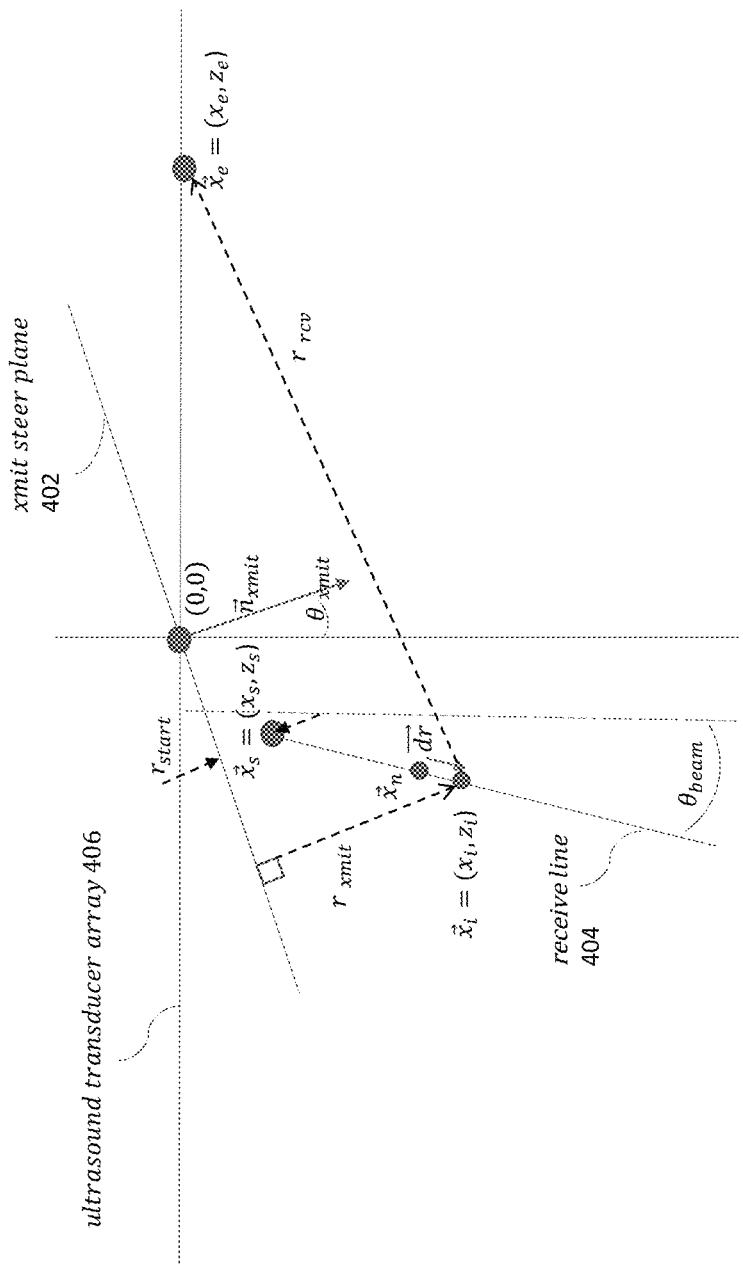
FIG. 4 illustrates a schematic diagram of example ultrasound transmission and reception, in accordance with certain embodiments described herein.

FIG. 4 illustrates a schematic diagram of example ultrasound transmission and reception, in accordance with certain embodiments described herein. FIG. 4 illustrates a transmit (xmit) steer plane 402, a receive line 404, and an ultrasound transducer array 406. A plane wave may be one example of the transmit steer plane 402, but any type of transmit beam may be used. The transmit angle is $\theta_{xmit}$ and the unit vector along $\theta_{xmit}$ is $\vec{n}_{xmit}$. The angle of the receive line 404 is $\theta_{beam}$. FIG. 4 illustrates three locations along the receive line 404, $\vec{x}_s$, $\vec{x}_n$, and $\vec{x}_i$. $\vec{x}_s$ is the shallowest (i.e., closest to the ultrasound transducer array 406) location along the receive line 404. $\vec{x}_i$ is the location from which a particular ultrasound wave is reflected. $\vec{x}_n$ is the location adjacent to $\vec{x}_i$ along the receive line 404 in the shallow direction. $\vec{dr}$ is a vector from $\vec{x}_n$ to $\vec{x}_i$, and may point from shallow to deep depths. The distance between adjacent locations along the receive line 404 (i.e., $\|dr\|$) may be dependent on the imaging depth and the total number of locations along the receive line 404. FIG. 4 further illustrates a location $\vec{x}_e$ on the ultrasound transducer array 406 where the ultrasound wave reflected from $\vec{x}_i$ is received. Referring still to FIG. 4:

$r_{xmit} = [\vec{x}_i, \vec{n}_{xmit}] = x_i * \sin(\theta_{xmit}) + z_i * \cos(\theta_{xmit})$, where $r_{xmit}$ is the distance from the transmit steer plane 402 to $\vec{x}_i$.

$\vec{x}_i = \vec{x}_s + m * \vec{dr}$, where m is the number of locations along the receive line 404 from $\vec{x}_s$ to $\vec{x}_i$. If the memory address for data collected from $\vec{x}_s$ is 0, then the memory address for data collected from $\vec{x}_i$ is m. Based on the above equations:

$r_{xmit} = [\vec{x}_s, \vec{n}_{xmit}]$, and by expansion and simplification:

$r_{xmit} = x_s * \sin(\theta_{xmit}) + z_s * \cos(\theta_{xmit}) + m * \|dr\| * (\sin(\theta_{xmit}) * \sin(\theta_{beam}) + \cos(\theta_{xmit}) * \cos(\theta_{beam}))$ $r_{xmit} = x_s * \sin(\theta_{xmit}) + z_s * \cos(\theta_{xmit}) + m * \|dr\| * \cos(\theta_{xmit} - \theta_{beam})$ $r_{xmit} = r_{start} + m * \|dr\| * \cos(\theta_{xmit} - \theta_{beam})$, where $r_{start}$ is the distance from the transmit steer plane 402 to $\vec{x}_s$. For simplicity, $\|dr\|$ will be written as dr.

The time-of-flight of an ultrasound wave from the transmit steer plane 402 to $\vec{x}_i$ and then from $\vec{x}_i$ to $\vec{x}_e$ is $\text{ToF}(\vec{x}_i, \vec{x}_e) = (r_{xmit} + r_{rcv})/c$, where $r_{rcv} = \sqrt{(x_i - x_e)^2 + (z_i - z_e)^2}$ is the distance from $\vec{x}_i$ to $\vec{x}_e$ and c is the speed of sound. Thus:

$c \cdot \text{ToF}(\vec{x}_i, \vec{x}_e) = r_{start} + m \cdot dr \cdot \cos(\theta_{xmit} - \theta_{beam}) + \sqrt{(x_i - x_e)^2 + (z_i - z_e)^2}$ Because $\vec{x}_i = \vec{x}_s + m \cdot \vec{dr}$,
$x_i = x_s + m \cdot dr \cdot \sin(\theta_{beam})$ and
$z_i = z_s + m \cdot dr \cdot \cos(\theta_{beam})$ $c \cdot \text{ToF}(\vec{x}_i, \vec{x}_e) = r_{start} + m \cdot dr \cdot \cos(\theta_{xmit} - \theta_{beam}) + \sqrt{(x_s + m \cdot dr \cdot \sin(\theta_{beam}) - x_e)^2 + (z_s + m \cdot dr \cdot \cos(\theta_{beam}) - z_e)^2}$ For simplicity, $\text{ToF}(\vec{x}_i, \vec{x}_e)$ will be written as ToF. Based on the above equation:

$(c \cdot \text{ToF} - r_{start} - m \cdot dr \cdot \cos(\theta_{xmit} - \theta_{beam}))^2 = (x_s + m \cdot dr \cdot \sin(\theta_{beam}) - x_e)^2 + (z_s + m \cdot dr \cdot \cos(\theta_{beam}) - z_e)^2$ Letting $\alpha = c \cdot \text{ToF} - r_{start}$:

$\alpha^2 - 2 \cdot \alpha \cdot m \cdot dr + m^2 \cdot dr^2 \cdot \cos(\theta_{xmit} - \theta_{beam})^2 = (x_s - x_e)^2 + 2 \cdot m \cdot dr \cdot \sin(\theta_{beam}) \cdot (x_s - x_e) + m^2 \cdot dr^2 \cdot \sin(\theta_{beam})^2 + (z_s - z_e)^2 + 2 \cdot m \cdot dr \cdot \cos(\theta_{beam}) \cdot (z_s - z_e) + m^2 \cdot dr^2 \cdot \cos(\theta_{beam})^2$ $dr^2 \cdot (\cos(\theta_{xmit} - \theta_{beam})^2 - 1) \cdot m^2 - (2 \cdot dr \cdot (\alpha + \sin(\theta_{beam}) \cdot (x_s - x_e) + \cos(\theta_{beam}) \cdot (z_s - z_e))) \cdot m + \alpha^2 + (x_s - x_e)^2 + (z_s - z_s)^2 = 0$ Letting $A = dr^2 \cdot (\cos(\theta_{xmit} - \theta_{beam})^2 - 1), B = -(2 \cdot dr \cdot (\alpha + \sin(\theta_{beam}) \cdot (x_s - x_e) + \cos(\theta_{beam}) \cdot (z_s - z_e)))$ and $C = \alpha^2 + (x_s - x_e)^2 + (z_s - z_s)^2$ Using the quadrature formula, where A ≠ 0, m can be found as:

$$m = \frac{-B \pm \sqrt{B^2 - 4AC}}{2A},$$

note that only the positive m is acceptable.

For the purpose of illustration, if it is assumed that $\theta_{xmit} = \theta_{beam}$, then A=0 and therefore m can be calculated as the following:

$$m = \frac{\alpha^2 + (x_s - x_e)^2 + (z_s - z_s)^2}{2 \cdot dr \cdot (\alpha + \sin(\theta_{beam}) \cdot (x_s - x_e) + \cos(\theta_{beam}) \cdot (z_s - z_e))}.$$

The above equation relates m to $x_s$, $z_s$, $x_e$, $z_e$, $\theta_{beam}$, dr, c, $r_{start}$, and ToF. For a particular receive line 404, the location of the first location ($x_s$, $z_s$) along the receive line 404 and the distance $r_{start}$ of this location from the transmit steer plane 402 may be known. The location ($x_e$, $z_e$) on the ultrasound transducer array 406 where the particular ultrasound data sample is received may also be known. For a given ultrasound transmit event, $\theta_{beam}$ may be known. For a given imaging depth and the total number of locations along the receive line 404, dr may be known. c, the speed of sound in the medium, may be known. The beamforming circuitry 300 may determine ToF based on the time after the ultrasound transmit when the particular ultrasound data sample is received. Thus, all the parameters needed to calculate m for a particular ultrasound data sample may be known.

The PoS calculator block 302 may use the above equation to calculate m for a particular ultrasound data sample using, among other parameters, the ToF of the ultrasound data sample as an input. Calculating m may be considered calculating the position in space $\vec{x}_i$ from which the ultrasound data was collected, because $\vec{x}_i = \vec{x}_s + m \cdot \vec{dr}$. m itself may be the memory address to be updated with the ultrasound data sample, so calculating m may also be considered calculating the memory address to be updated with the ultrasound data sample. However, as described above, m may be a non-integer value, such that the calculated memory address may not be an actual available location. Thus, calculating a memory address to be updated with the ultrasound data sample may include calculating an m value for an ultrasound data sample, interpolating the ultrasound data sample with another ultrasound data sample based on their two non-integer memory address (m) values, and updating a memory address having an integer value with the interpolated ultrasound data. The ToF for each position in the receive line space represented by an actual memory address may be predetermined based on the operating clock of the ultrasound device, the clock rate of the ADCs 124 in the receive datapath, and the decimation factor used by the receive datapath.

It should be appreciated that calculating the position in the receive line space may involve only a single equation, despite the position being in two-dimensions. This equation may be advantageous in comparison with using two equations to explicitly calculate the x and z components of the position. For example, when circuitry for solving this equation is implemented in hardware, the amount of hardware needed may be less than if the circuitry needed to solve two equations for the two variables x and z.

It should be appreciated that the ultrasound data sample from one receive datapath may be used to update multiple receive lines in multiple instances of the beamforming circuitry 300 and/or any samples on a grid using pixel-based beamforming. For example, for forming an image of x (axial) by y (lateral) pixels, one ultrasound data sample from a receive datapath may contribute to y locations in the lateral direction.

In other beamforming systems that lack the PoS calculator 302, as each receive datapath is multiplexed to the beamforming system, data from the receive datapath may be buffered by the beamforming system. A ToF may be calculated for each position along a particular receive line, or more particularly, for each memory address corresponding to each position. In other words, ToF may be calculated using a given memory address as the input. The buffered data that arrived at each calculated ToF may then be pulled from the buffer and associated with the position along the receive line, or more particularly, used to update the memory address, corresponding to that ToF. However, in the beamforming circuitry 300, the PoS calculator block 302 may directly calculate the position in the receive line space, or more particularly, the memory address corresponding to the position, for a received ultrasound data sample based on the ToF for that ultrasound data sample. In other words, the beamforming circuitry may calculate a memory address using a given ToF as the input. This may be done without initially buffering an ultrasound data sample from a receive datapath when the receive datapath is multiplexed to the beamforming circuitry 300. The output sample pipeline block 308 may then associate the ultrasound data sample with that position (in particular, with a memory address corresponding to that location) in the output receive line buffer block 310.

Figure 5:
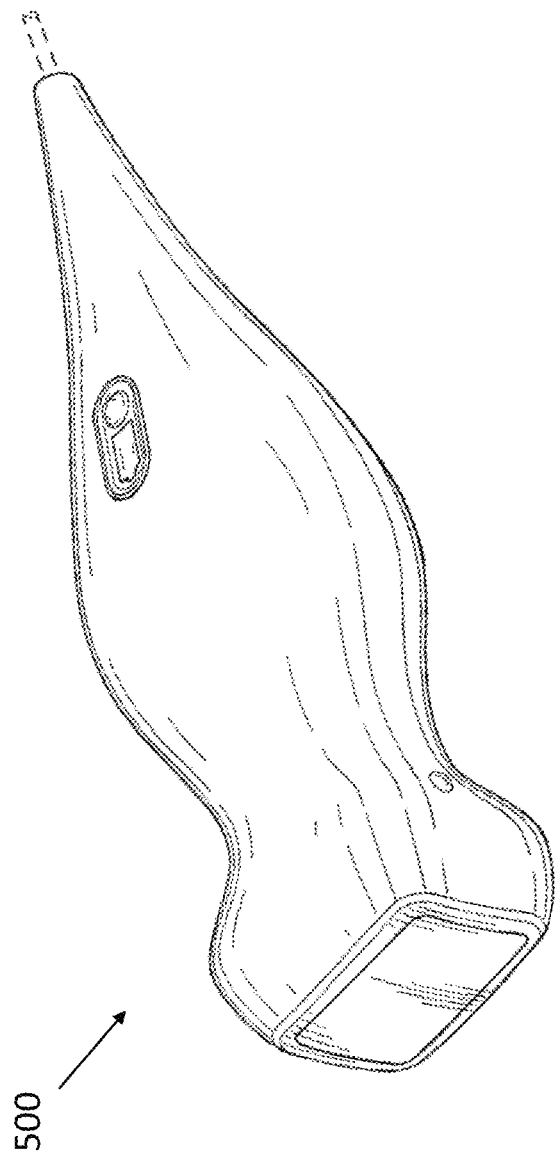
FIG. 5 illustrates an example handheld ultrasound probe in which the beamforming circuitry of FIG. 3 may be disposed, in accordance with certain embodiments described herein.

FIG. 5 illustrates an example handheld ultrasound probe 500 in which the beamforming circuitry 300 may be disposed, in accordance with certain embodiments described herein.

Figure 6:
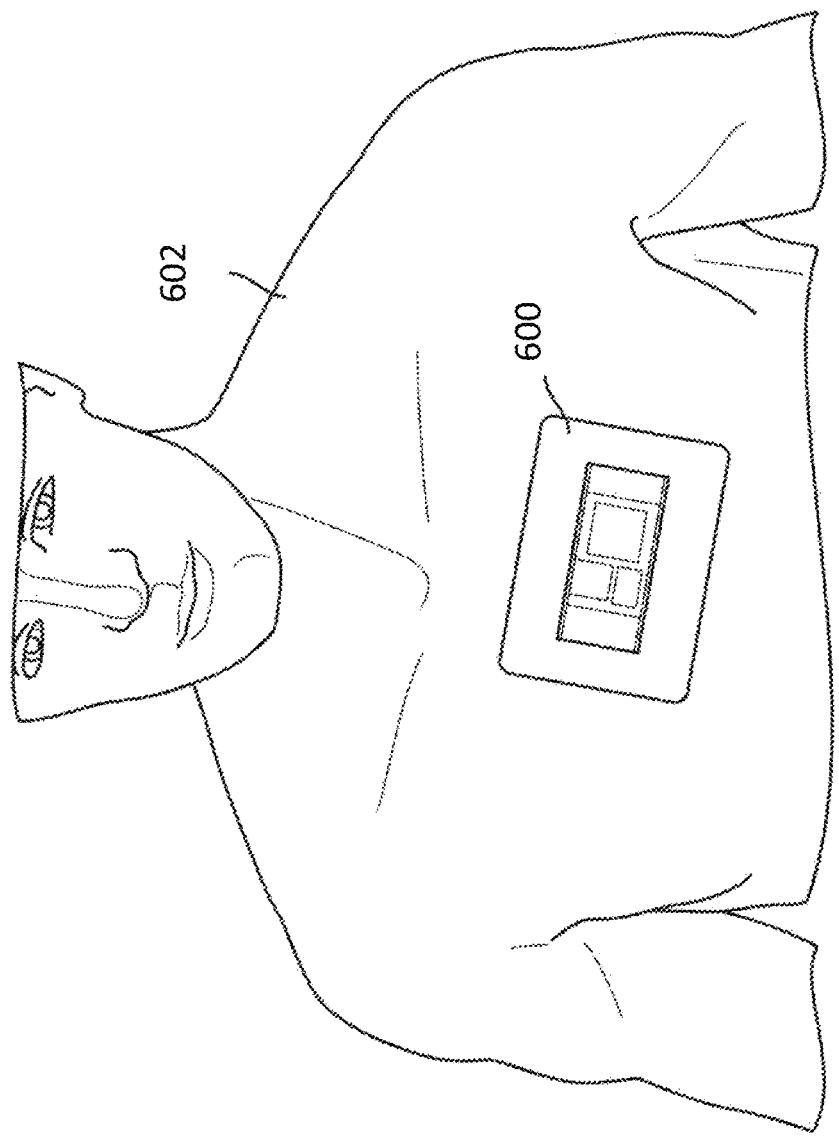
FIG. 6 illustrates an example ultrasound patch in which the beamforming circuitry of FIG. 3 may be disposed, in accordance with certain embodiments described herein.

FIG. 6 illustrates an example ultrasound patch 600 in which in which the beamforming circuitry 300 may be disposed, in accordance with certain embodiments described herein. The ultrasound patch 600 is coupled to a subject 602.

Figure 7:
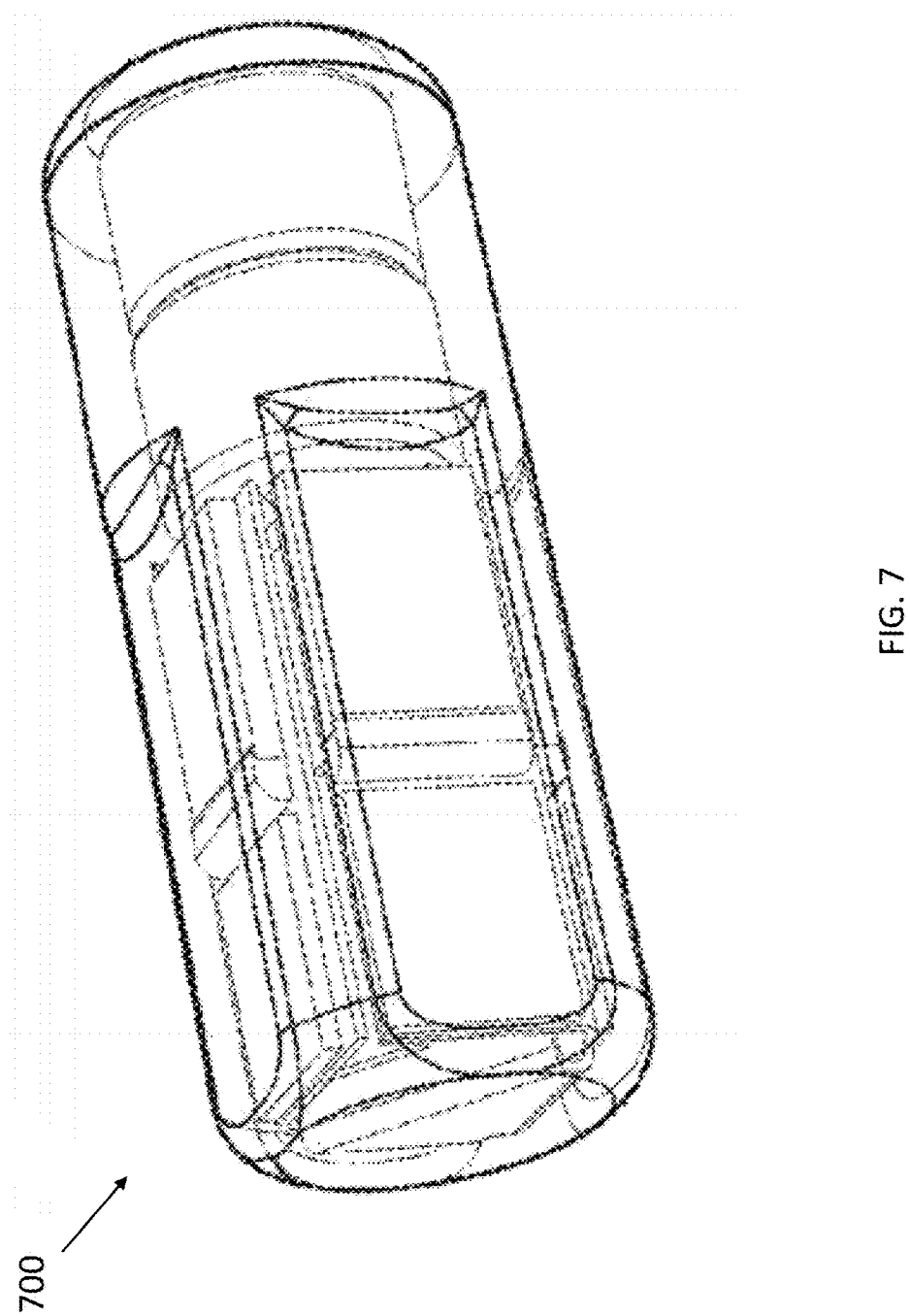
FIG. 7 illustrates an example ultrasound pill in which the beamforming circuitry of FIG. 3 may be disposed, in accordance with certain embodiments described herein.

FIG. 7 illustrates an example ultrasound pill 700 in which the beamforming circuitry 300 may be disposed, in accordance with certain embodiments described herein.

Some aspects relate to a method of processing ultrasound data, comprising calculating, with beamforming circuitry, a position in receive line space from which an ultrasound data sample was collected using a time-of-flight of the ultrasound data sample as an input.

In some embodiments, the method omits buffering the ultrasound data sample prior to the calculating.

In some embodiments, the method further includes receiving, with the beamforming circuitry, the ultrasound data sample from a receive datapath.

In some embodiments, the receive datapath comprises an ultrasound transducer, a transimpedance amplifier, analog processing circuitry, and an analog-to-digital converter.

In some embodiments, the time-of-flight of the ultrasound data sample comprises a time from transmission of an ultrasound wave from an ultrasound device to a time that a reflected ultrasound wave is received by the ultrasound device.

In some embodiments, the method further includes when calculating the position in the receive line space from which the ultrasound data sample was collected using the time-of-flight of the ultrasound data sample as the input, using the beamforming circuitry to calculate a non-integer memory address of a memory using the time-of-flight of the ultrasound data sample as the input; interpolate the ultrasound data sample with another ultrasound data sample to produce a single interpolated ultrasound data value; and update an actual memory address in the memory with the interpolated ultrasound data value.

In some embodiments, memory addresses in the memory are allocated based on position in space.

In some embodiments, each memory address in the memory represents a position in space that that is a distance depth/N away from a position represented by a previous memory address, wherein there are N memory addresses for a particular receive line, and wherein depth is an imaging depth.

In some embodiments, when updating the actual memory address with the interpolated ultrasound data value, the beamforming circuitry accumulates the interpolated ultrasound data value at the actual memory address.

In some embodiments, when accumulating the interpolated ultrasound data value at the actual memory address, the beamforming circuitry accumulates data received from a same spatial location by different ultrasonic transducer elements and/or compound current receive lines with next receive lines coherently.

In some embodiments, the beamforming circuitry calculates the position in the receive line space from which the ultrasound data sample was collected using the time-of-flight of the ultrasound data sample as the input using a single equation.

Some aspects relate to a method of processing ultrasound data, comprising calculating, using beamforming circuitry, a memory address to be updated with an ultrasound data sample using a time-of-flight of the ultrasound data sample as an input.

In some embodiments, the beamforming circuitry calculates the memory address without buffering the ultrasound data sample.

In some embodiments, the method includes receiving, with the beamforming circuitry, the ultrasound data sample from a receive datapath.

In some embodiments, the receive datapath comprises an ultrasound transducer, a transimpedance amplifier, analog processing circuitry, and an analog-to-digital converter.

In some embodiments, the time-of-flight of the ultrasound data sample comprises a time from transmission of an ultrasound wave from an ultrasound device to a time that a reflected ultrasound wave is received by the ultrasound device.

In some embodiments, when calculating the memory address to be updated with the ultrasound data sample using the time-of-flight of the ultrasound data sample as the input, the beamforming circuitry calculates a non-integer memory address using the time-of-flight of the ultrasound data sample as the input; interpolates the ultrasound data sample with another ultrasound data sample to produce a single interpolated ultrasound data value; and updates an actual memory address with the interpolated ultrasound data value.

In some embodiments, memory addresses in a memory are allocated based on position in space.

In some embodiments, each memory address in the memory represents a position in space that that is depth/N away from a position represented by a previous memory address, wherein there are N memory addresses for a particular receive line, and wherein depth is an imaging depth.

In some embodiments, when updating the actual memory address with the interpolated ultrasound data value, the beamforming circuitry accumulates the interpolated ultrasound data value at the actual memory address.

In some embodiments, when accumulating the interpolated ultrasound data value at the actual memory address, the beamforming circuitry accumulates data received from a same spatial location by different ultrasonic transducer elements and/or compound current receive lines with next receive lines coherently.

In some embodiments, the beamforming circuitry calculates the memory address to be updated with the ultrasound data sample based on the time-of-flight of the ultrasound data sample using a single equation.

Some aspects relate to a method of processing ultrasound data, comprising multiplexing, using beamforming circuitry, between multiple receive datapaths without buffering ultrasound data samples from the multiple receive datapaths.

Further description of the handheld ultrasound probe 500, the ultrasound patch 600, and the ultrasound pill 700 may be found in U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application), which is incorporated by reference herein in its entirety.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
a memory including a plurality of memory addresses; and
beamforming circuitry configured to:
calculate a position in receive line space for each ultrasound data sample of a plurality of ultrasound data samples collected using a time-of-flight of the ultrasound data samples as an input based on a determined time-of-flight for each ultrasound data sample of the plurality of ultrasound data samples, wherein the beamforming circuitry is not configured to buffer the ultrasound data sample prior to calculating the position in receive line space from which the ultrasound data sample was collected;
generate an integer interpolated ultrasound data value relating to the calculated position of each ultrasound data sample by interpolating a first non-integer ultrasound data sample of the plurality of ultrasound data samples from a first position around a position in the receive line space represented by a first memory address of the plurality of memory addresses, and interpolating a second non-integer ultrasound data sample of the plurality of ultrasound data samples from a second position around the position in the receive line space represented by the first memory address of the plurality of memory addresses, wherein the first non-integer ultrasound data sample and the second non-integer ultrasound data sample do not correspond to an actual memory address; and
wherein the beamforming circuitry is configured, when calculating the position in the receive line space from which the ultrasound data sample was collected using the time-of-flight of the ultrasound data sample as the input, to:
calculate a first non-integer memory address using the time-of-flight of the ultrasound data sample as the input for a first of two ultrasound data samples of the plurality of ultrasound data samples from two different positions;
calculate a second non-integer memory address using the time-of-flight of the ultrasound data sample as the input for a second of two ultrasound data samples of the plurality of ultrasound data samples from the two different positions; and
store the integer interpolated ultrasound data value at the first memory address in the memory.

2. The apparatus of claim 1, wherein the beamforming circuitry is configured to receive the ultrasound data sample from a receive datapath.

3. The apparatus of claim 2, wherein the receive datapath comprises an ultrasound transducer, a transimpedance amplifier, analog processing circuitry, and an analog-to-digital converter.

4. The apparatus of claim 1, wherein the time-of-flight of the ultrasound data sample comprises a time from transmission of an ultrasound wave from an ultrasound device to a time that a reflected ultrasound wave is received by the ultrasound device.

5. The apparatus of claim 1, wherein memory addresses in the memory are allocated based on a position in space.

6. The apparatus of claim 1, wherein each memory address in the memory represents a position in space that is a distance depth/N away from a position represented by a previous memory address, wherein there are N memory addresses for a particular receive line, and wherein depth is an imaging depth.

7. The apparatus of claim 1, wherein the beamforming circuitry is configured, when storing the integer interpolated ultrasound data value at the first memory address, to at least one of store an ultrasound data sample received from a same spatial location by different ultrasonic transducer elements or compound current receive lines with next receive lines coherently.

8. The apparatus of claim 1, wherein the beamforming circuitry is configured, when calculating the position in the receive line space from which the ultrasound data sample was collected using the time-of-flight of the ultrasound data sample as the input, to use a single equation.

9. An apparatus, comprising:
a memory including a plurality of memory addresses; and
beamforming circuitry configured to:
calculate a first memory address corresponding to an ultrasound data sample of a plurality of ultrasound data samples using a time-of-flight of the ultrasound data samples as an input based on a determined time-of-flight for each ultrasound data sample of the plurality of ultrasound data samples, wherein the beamforming circuitry is not configured to buffer the ultrasound data sample prior to calculating the first memory address to be updated with the ultrasound data sample;
generate an integer interpolated ultrasound data value relating to the calculated first memory address of the corresponding ultrasound data sample by interpolating a first ultrasound data sample of the plurality of ultrasound data samples having a first non-integer memory addresses around the first memory address of the plurality of memory addresses, and interpolating a second ultrasound data sample of the plurality of ultrasound data samples having a second non-integer memory address around the first memory address of the plurality of memory addresses, wherein the first non-integer memory address and the second non-integer memory address do not correspond to an actual memory address; and
wherein the beamforming circuitry is configured, when calculating the position in the receive line space from which the ultrasound data sample was collected using the time-of-flight of the ultrasound data sample as the input, to:
calculate the first non-integer memory address using the time-of-flight of the ultrasound data sample as the input for a first of two ultrasound data samples of the plurality of ultrasound data samples from two different positions;
calculate the second non-integer memory address using the time-of-flight of the ultrasound data sample as the input for a second of two ultrasound data samples of the plurality of ultrasound data samples from the two different positions; and
store the integer interpolated ultrasound data value at the first memory address in the memory.

10. The apparatus of claim 9, wherein the beamforming circuitry is configured to receive the ultrasound data sample from a receive datapath.

11. The apparatus of claim 10, wherein the receive datapath comprises an ultrasound transducer, a transimpedance amplifier, analog processing circuitry, and an analog-to-digital converter.

12. The apparatus of claim 9, wherein the time-of-flight of the ultrasound data sample comprises a time from transmission of an ultrasound wave from an ultrasound device to a time that a reflected ultrasound wave is received by the ultrasound device.

13. The apparatus of claim 9, where the beamforming circuitry is configured, when calculating the memory address to be updated with the ultrasound data sample using the time-of-flight of the ultrasound data sample as the input, to:
store the integer interpolated ultrasound data value at the memory address in the memory.

14. The apparatus of claim 13, wherein the plurality of memory addresses in a memory are allocated based on a position in space.

15. The apparatus of claim 13, wherein each memory address in the memory represents a position in space that is depth/N away from a position represented by a previous memory address, wherein there are N memory addresses for a particular receive line, and wherein depth is an imaging depth.

16. The apparatus of claim 13, wherein the beamforming circuitry is configured, when updating the memory address with the interpolated ultrasound data value, to accumulate the integer interpolated ultrasound data value at the memory address.

17. The apparatus of claim 16, wherein the beamforming circuitry is configured, when accumulating the integer interpolated ultrasound data value at the actual memory address, to at least one of accumulate data received from a same spatial location by different ultrasonic transducer elements or compound current receive lines with next receive lines coherently.

18. The apparatus of claim 9, wherein the beamforming circuitry is configured, when calculating the memory address to be updated with the ultrasound data sample based on the time-of-flight of the ultrasound data sample, to use a single equation.

* * * * *